(12) United States Patent
Bellm et al.

(10) Patent No.: US 6,710,867 B2
(45) Date of Patent: Mar. 23, 2004

(54) DEVICE AND METHOD FOR INSPECTING A THREE-DIMENSIONAL SURFACE STRUCTURE

(75) Inventors: Hubert Bellm, Stutensee (DE); Dieter Kant, Rheinstetten (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/095,005

(22) Filed: Mar. 12, 2002

(65) Prior Publication Data

US 2002/0180962 A1 Dec. 5, 2002

Related U.S. Application Data

(63) Continuation of application No. PCT/DE00/02855, filed on Aug. 22, 2000.

(30) Foreign Application Priority Data

Sep. 13, 1999 (DE) .................................... 299 16 075 U

(51) Int. Cl.[7] .............................................. G01N 21/88
(52) U.S. Cl. ................................................... 356/237.1
(58) Field of Search ................. 356/237.1, 237.2–237.5

(56) References Cited

U.S. PATENT DOCUMENTS

| 3,824,387 A | * | 7/1974 | Garst | .......................... 700/74 |
| 3,902,811 A | | 9/1975 | Altman et al. | |
| 5,206,705 A | | 4/1993 | Tokura | |
| 5,619,587 A | | 4/1997 | Willoughby, Jr. et al. | |
| 6,181,474 B1 | * | 1/2001 | Ouderkirk et al. | .......... 356/399 |

FOREIGN PATENT DOCUMENTS

| DE | 4410603 C1 | 6/1995 |
| DE | 19608468 A1 | 9/1997 |
| DE | 19713521 A1 | 10/1998 |
| DE | 19915052 A1 | 10/2000 |
| EP | 0403908 A2 | 12/1990 |
| EP | 0866308 A2 | 9/1998 |

\* cited by examiner

*Primary Examiner*—Richard A. Rosenberger
(74) *Attorney, Agent, or Firm*—Sughrue Mion, PLLC

(57) ABSTRACT

An inspection device for inspecting the solder paste printing on printed circuit boards. Three-dimensional surface structures (19) are optically detected (7) and the values of their geometric properties are calculated. The values thus measured are inspected (29) for conformance to an absolute tolerance range. To fine-adjust the limit values, an operator has the option of evaluating the displayed defects as pseudo-defects, in which case the measured values are automatically accepted as the new limit values of the respective absolute tolerance range.

8 Claims, 1 Drawing Sheet

DEVICE AND METHOD FOR INSPECTING A THREE-DIMENSIONAL SURFACE STRUCTURE

This is a Continuation of International Application PCT/DE00/02855, with an international filing date of Aug. 22, 2000, which was published under PCT Article 21(2) in German, and the disclosure of which is incorporated into this application by reference.

FIELD OF AND BACKGROUND OF THE INVENTION

The invention relates generally to a device for inspecting a three-dimensional structure and more particularly to a device for inspecting three-dimensional printed circuit boards. The invention additionally relates to a surface structure inspection method.

A conventional device for inspecting a three-dimensional surface structure is known from German Patent Specification DE 196 08 468 C2. The device described in this German patent specification is suitable for inspecting a three-dimensional surface structure of a substantially flat test piece. In particular, the device is directed to inspecting the solder paste printing on printed circuit boards. Using an optical sensor, a partial area of the surface of the test piece is measured in three dimensions. A positioning device is used to position the optical sensor relative to the test piece, such that different partial areas of the surface are successively inspected.

One application in which the above-mentioned conventional device can be used is for inspection of the solder paste printing on printed circuit boards. To prevent potential solder defects from being transferred throughout the entire process chain in the production of electronic printed circuit boards, which would require subsequent repair of the boards at a substantial cost, the solder paste printing process must be constantly monitored. Monitoring the printing process enables the detection of defects caused by screen printing prior to the insertion of components on the printed circuit board and segregation of defective boards before additional costs are incurred.

Printed circuit boards for surface-mounted components, so-called surface mount technology (SMT) boards, are produced in large quantities and with many variations. The surface mounted components are fixed to the printed circuit board by soldering their terminals to "metallized" surfaces, referred to as pads, and are thereby also electrically connected with the printed conductors on the printed circuit board. For this purpose, a pattern of metallic pads corresponding to the position of the terminals of the components is provided on the printed circuit board. Solder paste is then deposited on the pads using a screen printing process. Thereafter, the surface mount component is mounted onto the printed circuit board. The component is initially held to the board by the adhesive property of the solder paste. Subsequently, after heating the printed board assembly, the terminals of the components are permanently soldered to the pads.

In the area of packaging technology, the trend is toward ever-increasing integration of the components with an increasing number of terminals per component housing. In the so-called fine-pitch range, the distance between two adjacent component terminals is approximately $1/40$ of an inch. As a result, the pads on the printed circuit boards are also becoming smaller and more dense. About 80 percent of solder defects in the fine-pitch range are caused by solder paste printing. Examples of such defects are: insufficient solder paste deposit and short-circuits between adjacent pads due to inexact placement of the screen printing template during solder paste printing. To detect these defects, and to locate weak points in the production process, the printed circuit board is optically inspected after the solder paste has been deposited.

A second conventional device, described in German patent application number 199 15 052.4, comprises a device for inspecting a three-dimensional surface structure and a process for calibrating the device. This conventional inspection device is distinguished by improved accuracy in measuring three-dimensional surface structures. According to German patent application number 199 15 052.4, the coordinates of the characteristics to be inspected, particularly the solder deposit on printed circuit boards, can be derived from the mounting data of the components, which are normally available in the form of an electronic file after the design process of the components has been completed on a CAD design tool. One drawback to this conventional device, however, is that the user must manually calculate limit values for the geometric properties or the characteristics of the solder paste deposit and enter these values into the inspection device using a keyboard. In addition, the operator must manually enter the values for adjustments during any setup process. This work is very time-consuming and thus costly.

OBJECTS OF THE INVENTION

One object of the present invention is to provide a device and method for inspecting a three-dimensional surface structure in which the definition of limit values to which the measured values of the geometric properties of an inspected surface structure must conform is simplified for the operator.

SUMMARY OF THE INVENTION

To attain the above and other objects, a novel device and method in accordance with the present invention are proposed.

In accordance with one embodiment of the invention, a device is provided for inspecting a three-dimensional surface structure of a substantially flat test piece, the device includes an optical sensor operable to detect, in three-dimensions, at least a partial area of the surface of the test piece, a positioning device operable to position the optical sensor and the test piece relative to one another, a first memory operable to store setpoint values associated with geometric properties of the surface structure, a second memory operable to store tolerance values indicating a relative tolerance range for the geometric properties, an arithmetic logic unit operable to calculate limit values of an absolute tolerance range, and a display unit operable to display a defect if a measured value of at least one of the geometric properties of at least one of the inspected surface structures does not fall within a respective range of the absolute tolerance range.

In accordance with another embodiment of the invention, a surface structure inspection method is provided that includes generating a measured value by measuring a geometric property of a three-dimensional surface structure, calculating a limit value of an absolute tolerance range from a stored setpoint value for the geometric property and a stored relative tolerance value for the geometric property, comparing the measured value and the limit value, and generating a defect indication if the measured value fails to lie within the limit value.

In accordance with another embodiment of the invention, a device for inspecting the surface of a three-dimensional structure is provided which includes a first memory operable to store setpoint values for geometric properties of the three-dimensional structure, a second memory operable to store relative tolerance values corresponding to the setpoint values, and a logic unit operable to automatically calculate absolute tolerance values for the geometric properties, wherein the absolute tolerance values are based on respective values of the stored relative tolerance values and the stored setpoint values.

Also, a device and method in accordance with an embodiment of the present invention has the advantage that the process of defining the limit values, as discussed above, requires substantially less time than the time required for conventional devices. Accordingly, inspection of the solder paste printing on printed circuit boards in accordance with the present invention is less costly.

According to one embodiment, the limit values of the geometric properties of the solder paste deposit are calculated by a computer program that can be integrated into the control computer of the inspection device. As a result, the user of the inspection device is no longer required to perform time-consuming manual calculations.

A device and method in accordance with this embodiment of the present invention is advantageous particularly for inspecting the solder paste deposit on a printed circuit board. One reason this advantage is realized is because this type of inspection requires inspection of many different geometric properties and, thus, many different limit values need to be calculated.

According to one variant of the present embodiment, the operator can track the execution of the inspection program and the results of the individual inspection steps with an output device that outputs the measured values of the geometric properties of an inspected surface structure. For example, a display screen displays the measured values of the geometric properties and for those values that fall outside their absolute tolerance range, the values can be highlighted on the screen, particularly by their color, in contrast to the measured values of other geometric properties that fall within their absolute tolerance range. Accordingly, the operator's attention is drawn directly to any possible defects.

According to a further embodiment, automatic correction of the limit values is advantageously achieved by (i) an input unit that the operator can use to specify whether a measured value of a geometric property that falls outside the absolute tolerance range should be evaluated as a defect and by (ii) an arithmetic logic unit that will adapt the absolute tolerance range of the geometric property according to the measured value if that value is not evaluated as a defect. This correction ensures ready adaptability of the inspection to any changes in the parameters of a production process. The operator is relieved of the manual entry of many numbers during the setup process. Also, the new limit values can be used as the basis of subsequent inspection steps.

To improve the decision basis for the subjective evaluation by the operator, a height image of the surface structure to be inspected may be recorded with the optical sensor and displayed on a screen. The height image is characterized by a particularly useful graphical appearance on the screen. The operator thus has access to all the information contained in the height image. As a result, the operator has a better decision basis than he or she would have had if the decision were based solely on the values of the optical properties of the surface structure to be inspected as measured by other image analysis processes.

BRIEF DESCRIPTION OF THE DRAWINGS

The invention as well as embodiments and advantages thereof will now be described in greater detail with reference to the figures, in which.

DETAILED DESCRIPTION OF THE PREFERRED EMBODIMENTS

Figure 1:
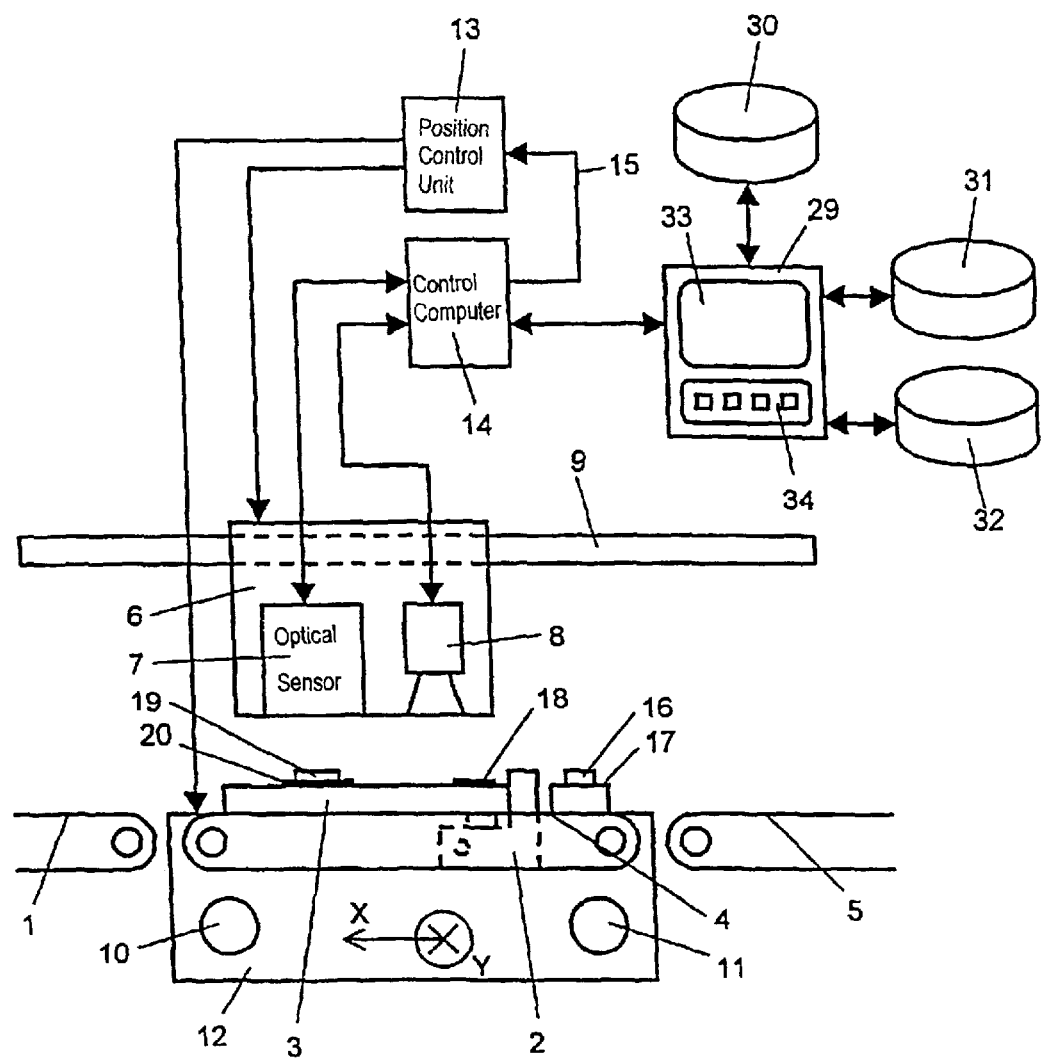
FIG. 1 is a diagrammatic view of an exemplary embodiment of the invention.

An inspection device, the principle structure of which is depicted in FIG. 1, can be integrated into a printed circuit board production line. Uninspected printed circuit boards are fed to the inspection device by a conveyor belt 1. A tippable stopper 2, the hidden parts of which are indicated by dashed lines, holds each printed circuit board 3 to be inspected in an inspection position. After inspection is complete, the stopper 2 is downwardly retracted and the printed circuit board 3 is transported out of the inspection device by a conveyor belt 4 and to another processing station (not shown) by a conveyor belt 5.

In practice, several printed circuit boards are usually combined in a panel and are jointly moved within the production line by a conveying mechanism. FIG. 1 shows only a single circuit board 3, for the sake of clarity. However, it is recognized that the device depicted in FIG. 1 could also operate on a panel of combined printed circuit boards.

The axes of the machine coordinates of the inspection device are indicated by arrows X and Y. The orientation of arrow Y is at a right angle to arrow X and points into the drawing plane. Above printed circuit board 3, there is a sensor unit 6 including an optical sensor 7, which is embodied here as a confocal microscope, and a CCD camera 8. To enable the sensor unit 6 to be positioned over any point on the printed circuit board 3 for the inspection of the features to be inspected, the sensor unit can be displaced in the X direction on a guide shaft 9. A printed circuit board holder is arranged on a carriage 12, which is supported on two shafts 10 and 11 so as to be displaceable in the Y direction.

Drive motors (not shown) of the sensor unit 6 and the carriage 12 are controlled by a position control unit 13 in such a way that they approach position setpoint values communicated on line 15. The position setpoint values are specified by a control computer 14. Position control unit 13, carriage 12 and the corresponding guide shafts 9 and 10–11 thus constitute a positioning device with which the sensor unit 6 and the test piece 3 can be positioned in any manner relative to one another with respect to the X–Y coordinates.

To calibrate the inspection device, carriage 12 has a calibration mark 16 which is independent of the test piece 3 and is permanently connected with the inspection device. Calibration mark 16 is embodied here as a cylinder standing on a plane 17. In this embodiment calibration mark 16 has a diameter of 1 mm and protrudes 0.4 mm above plane 17. An upper circular surface of the calibration mark 16 is blackened, in order to improve the contrast for the gray-scale values. With the aid of the calibration mark 16 and a cross mark 18 located on the printed circuit board 3 and a second cross mark in the left rear area of the printed circuit board 3 (not shown), the optical sensor 7 and the CCD camera 8, after calibration is complete, can be exactly positioned over the features to be inspected, and the geometric dimensions and the positions of the features can be measured.

As an example of a surface structure to be inspected, a solder deposit 19 is shown on the printed circuit board 3. Solder deposit 19 is applied to a metallic solder pad 20 during a solder paste deposition process. An arithmetic logic unit 29, provided with a screen display 33 and a keyboard input 34, is used to operate the inspection device during calibration and fine adjustment processes as well as for the actual inspection process. Present states of the inspection device and the inspection results can be displayed on the screen display 33, and the required operator inputs can be made with the aid of the keyboard 34.

Setpoint values for geometric properties of the surface structure to be inspected are stored in a first memory 30. In this embodiment the setpoint values include, among others, pad data, e.g., for pad 20, which can be obtained from the CAD data of the printed circuit board 3 using a CAD converter. Since the thickness of the screen printing template used during the solder paste deposition process cannot typically be obtained from the CAD data, this data is entered as a parameter by the operator using the keyboard 34. Also input are any required reduction factors for the template openings.

Also, the thickness of the solder resist is required for parameterizing the image processing algorithms. With this information, an edge search algorithm can, for instance, distinguish between an edge of a terminal area and an edge of the solder resist. Using the pad data and the manually entered values, the theoretical characteristics for area, height, volume and coverage of the solder paste deposit on the pads are calculated as setpoint values.

In a second memory 31, values indicating the relative tolerance range for the geometric properties are stored. These values are assigned respectively to the individual theoretical characteristics. From the setpoint values in memory 30 and the values of the relative tolerance ranges in memory 31, the arithmetic logic unit 29 calculates the various limit values of absolute tolerance ranges, which are stored in a third memory 32. The memories 30, 31 and 32 are depicted separately in FIG. 1 for the sake of clarity. In practice, these memories can be located on the same storage medium.

To simplify entry of the template data, screen 33 of arithmetic logic unit 29 displays a mask with input fields for the template thickness in micrometers, the thickness of the solder resist in micrometers, a reduction factor of the template openings in the X direction, a reduction factor of the template openings in the Y direction, a center offset of the template openings in the X direction in micrometers, and a center offset of the template openings in the Y direction in micrometers. The manually entered template data is used to calculate the theoretical characteristics of the solder paste deposit. A useful auxiliary variable in this regard is the pad area. In a rectangular pad, for instance, the pad area is the product of the pad width and the pad length.

The area of the solder paste deposit on a pad is calculated as the product of the pad width, the reduction factor in the Y direction, the pad length, and the reduction factor in the X direction. The volume of the solder paste deposit is calculated as the product of the area and the template thickness. An absolute offset of the solder paste deposit in the X direction is equal to the amount of the entered center offset of the template openings in the X direction. An absolute offset in the Y direction corresponds to the entered amount of the center offset in the Y direction. In addition, a relative offset in the X direction is calculated as a theoretical setpoint value. This setpoint value is the quotient of the entered amount of the center offset in the X direction and the pad length. A relative offset in the Y direction is calculated as the quotient of the entered amount of the center offset in the Y direction and the pad width. Pad coverage is calculated as the quotient of the solder paste deposit area and the pad area.

From the setpoint values thus determined, which are stored in memory 30, and from the values of the relative tolerance ranges stored in memory 31, the arithmetic logic unit 29 calculates the values of the absolute tolerance ranges, which are stored in memory 32 in the following manner. A lower limit value of the solder paste area is equal to the product of the setpoint value of the paste area and the lower limit value of the relative tolerance range assigned to the paste area. Correspondingly an upper limit value of the paste area is calculated as the product of the setpoint value of the paste area and the upper limit value of the relative tolerance range for the paste area. Absolute tolerance ranges for height as a function of template thickness and volume as a function of the setpoint value of the paste volume are determined analogously.

An upper limit value for the absolute offset in the X direction is calculated as the sum of the setpoint value of the absolute offset in the X direction and the product of the pad length and a relative tolerance value of the offset. Correspondingly, an upper limit value for the absolute offset in the Y direction is calculated as the sum of the setpoint value of the absolute offset in the Y direction and the product of the pad width and a relative tolerance value of the offset. An upper and a lower limit value of the coverage is calculated from the setpoint value of the coverage and the associated relative tolerance ranges.

Due to the variability of the production process of the printed circuit board 3, which is not known in advance, the theoretically calculated limit values of the absolute tolerance ranges—as described above—which were stored in memory 32 must still be fine-adjusted for the inspection of the solder paste deposit. In this fine adjustment, the inspection device approaches and measures the individual surface structures to be inspected. If the inspection device detects a defect because the absolute tolerance range of a geometric property, e.g. the volume of the solder paste deposit on a pad, is exceeded, the occurrence of a defect is indicated on the screen display. In addition, the operator, by pressing a button, such as "display defect", can request the measured values of the geometric properties and the recorded height image as well as the gray scale picture of the solder paste deposit to be displayed on the screen 33.

The measured values that exceed the limit values of the absolute tolerance range are highlighted, e.g., by the color red, in contrast to the non-highlighted, e.g., green, values so the attention of the operator is directly drawn to these values. Based on the displayed measured values and pictures, the operator can decide whether the detected defect is a pseudo-defect or an actual defect. A defect is considered a pseudo-defect if the measured values of the geometric property must be defined as "good" or acceptable based on the variability of the production process even though the measured values fall outside the limit values of the absolute tolerance range.

The operator informs the arithmetic logic unit 29 of the inspection device of his decision by pushing a button such as "confirm error" or a button such as "ignore error" on the keyboard 34. Pushing one of these buttons triggers either an "actual defect" counter or a "pseudo-defect" counter, respectively. In addition, if the "ignore error" button is pushed, i.e., if the detected defect is a pseudo-defect, the limit value of the absolute tolerance range, which was previously stored in memory 32 and was exceeded by the measured value, is updated in memory 32, after a plausibility check, with a new limit value setting of the respective absolute tolerance range.

A complex manual entry of new limit values by the operator is thus not required. Furthermore, the inspection device thereafter tolerates measured values that correspond to this particular pseudo-defect. As such, the invention provides a semi-automatic training functionality of the inspection device, which largely relieves the operator from being required to make manual entries and for which the operator only needs to distinguish between pseudo-defects and actual defects. The correction of the values of the absolute tolerance range stored in memory 32 is accurately and automatically performed by the arithmetic logic unit 29.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. A device for inspecting a three-dimensional surface structure of a substantially flat test piece, the device comprising:

an optical sensor operable to detect, in three-dimensions, at least a partial area of the surface of the test piece;

a positioning device operable to position said optical sensor and the test piece relative to one another;

a first memory operable to store setpoint values associated with geometric properties of the surface structure;

a second memory operable to store tolerance values indicating a relative tolerance range for the geometric properties;

an arithmetic logic unit operable to calculate limit values of an absolute tolerance range;

a display unit operable to display a defect if a measured value of at least one of the geometric properties of at least one of the inspected surface structures does not fall within a respective range of the absolute tolerance range;

outputting means for outputting the measured value corresponding to one of the geometric properties of an inspected surface structure; and input means for inputting information regarding whether a measured value of a geometric property that does not fall within the absolute tolerance range should be evaluated as a defect;

wherein the arithmetic logic unit is configured such that when the measured value is not evaluated as a defect, the absolute tolerance range of the geometric property is adjusted corresponding to the measured value.

2. A device as claimed in claim 1 configured to inspect solder paste printing on a printed circuit board.

3. A device as claimed in claim 2, wherein the surface structure to be inspected is a solder paste deposit located on a terminal area for component connection on a printed circuit board and the geometric properties comprise at least one of an area, a height, and a volume of the solder paste deposit, and an offset of the solder paste deposit relative to the terminal area.

4. A device as claimed in claim 1, wherein the outputting means is a screen on which measured values of a geometric property that do not fall within a respective absolute tolerance range are highlighted.

5. A device as claimed in claim 4, wherein the highlighting is affected by using a particular color for the geometric properties that do not fall within their respective tolerances in contrast to measured values of other geometric properties that do fall within their respective absolute tolerance range.

6. A device as claimed in claim 1, wherein said optical sensor records a height image of the surface structure to be inspected and the height image or a gray scale image is displayed on the display unit.

7. A surface structure inspection method, comprising:

generating a measured value by measuring a geometric property of a three-dimensional surface structure;

calculating a limit value of an absolute tolerance range from a stored setpoint value for the geometric property and a stored relative tolerance value for the geometric property;

comparing the measured value and the limit value;

generating an defect indication if the measured value fails to lie within the limit value;

detecting a manually input signal used to evaluate the measured value as not indicative of a defect; and automatically updating the limit value of the absolute tolerance range to encompass the measured value.

8. A device for inspecting the surface of a three-dimensional structure, the device comprising:

a first memory operable to store setpoint values for geometric properties of the three-dimensional structure;

a second memory operable to store relative tolerance values corresponding to the setpoint values;

a logic unit operable to automatically calculate absolute tolerance values for the geometric properties, wherein the absolute tolerance values are based on respective values of the stored relative tolerance values and the stored setpoint values;

a measuring device operable to measure actual values for the geometric properties of the three-dimensional structure;

a comparator operable to compare the actual values and the absolute tolerance values;

a defect determiner operable to determine whether a result of the comparison of the actual values and the absolute tolerance values constitutes a defect;

an output device operable to highlight, with respect to corresponding absolute tolerance values, those actual values that result in a defect determination by said detect determiner; and an input device operable to receive manual input from an operator, wherein the manual input is used to determine whether the absolute tolerance value, corresponding to a defect, should be adjusted in accordance with the corresponding actual value.

* * * * *